United States Patent
Jayaraman

(10) Patent No.: US 11,103,252 B2
(45) Date of Patent: Aug. 31, 2021

(54) DEVICE TO TREAT VASCULAR DEFECT AND METHOD OF MAKING THE SAME

(71) Applicant: Swaminathan Jayaraman, Pleasanton, CA (US)

(72) Inventor: Swaminathan Jayaraman, Pleasanton, CA (US)

(*) Notice: Subject to any disclaimer, the term of this patent is extended or adjusted under 35 U.S.C. 154(b) by 222 days.

(21) Appl. No.: 16/254,042

(22) Filed: Jan. 22, 2019

(65) Prior Publication Data

US 2019/0223879 A1 Jul. 25, 2019

Related U.S. Application Data

(60) Provisional application No. 62/620,696, filed on Jan. 23, 2018.

(51) Int. Cl.
*A61B 17/12* (2006.01)
*A61F 2/07* (2013.01)
*A61F 2/90* (2013.01)
*A61F 2/82* (2013.01)
(Continued)

(52) U.S. Cl.
CPC .. *A61B 17/12113* (2013.01); *A61B 17/12168* (2013.01); *A61F 2/07* (2013.01); *A61F 2/90* (2013.01); *A61B 2017/00526* (2013.01); *A61B 2017/00867* (2013.01); *A61B 2017/1205* (2013.01); *A61F 2/848* (2013.01); *A61F 2002/823* (2013.01);
(Continued)

(58) Field of Classification Search
CPC .... A61F 2/07; A61F 2/90; A61F 2/848; A61F 2250/0048; A61F 2002/823; A61F 2220/0075; A61B 17/12113; A61B 17/12168; A61B 2017/00867; A61B 2017/00526
See application file for complete search history.

(56) References Cited

U.S. PATENT DOCUMENTS

| | | | | |
|---|---|---|---|---|
| 7,572,290 B2 * | 8/2009 | Yodfat | | A61F 2/07 623/1.15 |
| 7,857,844 B2 * | 12/2010 | Norton | | A61F 2/90 623/1.53 |
| 9,078,658 B2 * | 7/2015 | Hewitt | | A61B 17/12177 |

(Continued)

FOREIGN PATENT DOCUMENTS

| EP | 1374799 A1 | 1/2004 |
|---|---|---|
| EP | 1698907 A1 | 9/2006 |

OTHER PUBLICATIONS

Morris, L., F.Stefanov, N.Hynes, E.B.Diethrich, S.Sultan, "An Experimental Evaluation of Device/Arterial Wall Compliance Miismatch for Four Stent-Graft Devices and a Multi-layer Flow Modulator Device for the Treatment of Abdominal Aortic Aneurysms"; Eur. J. Vasc. Endovasc. Surg., (2016), pp. 44-55, 51.

(Continued)

*Primary Examiner* — Julian W Woo
(74) *Attorney, Agent, or Firm* — Shirley A. Recipon

(57) ABSTRACT

The device includes a braided component formed from a network of wires having at least two different diameters. The outer surface of the braided component has roughness from about 30 microns to about 90 microns and the wires of different diameters provide the desired porosity to the device. The network of wires includes a biocompatible shape memory alloy and a noble metal as a coating material.

20 Claims, 3 Drawing Sheets

(51) Int. Cl.
*A61B 17/00* (2006.01)
*A61F 2/848* (2013.01)

(52) U.S. Cl.
CPC . *A61F 2220/0075* (2013.01); *A61F 2240/001* (2013.01); *A61F 2250/0048* (2013.01)

(56) References Cited

U.S. PATENT DOCUMENTS

| | | | | |
|---|---|---|---|---|
| 10,335,297 | B2 * | 7/2019 | Vong | A61F 2/90 |
| 10,390,933 | B2 * | 8/2019 | Dickinson | A61M 1/3655 |
| 10,478,194 | B2 * | 11/2019 | Rhee | A61B 17/12172 |
| 2004/0215332 | A1 | 10/2004 | Frid | |
| 2005/0288770 | A1 | 12/2005 | Frid | |
| 2009/0270970 | A1 * | 10/2009 | Yodfat | A61F 2/07 |
| | | | | 623/1.11 |

OTHER PUBLICATIONS

Yassa, Eanas S. M.D., Joseph V. Lombardi, M.D., "Infrarenal EVAR Technology Review," Endovascular Today, Mar. 2012, pp. 38-44.
Rajah, Gary M.D., Sandra Narayanan, M.D., Leonardo Rangel-Castilla, M.D., "Update on flow diverters for the endovascular management of cerebral aneurysms," Neurosurg. Focus (2017) pp. 1-11 vol. 42 (6):E2; DOI: 10.3171/2017.3.FOCUS16427.
Abraham, Cherrie Z. M.D., Victor M. Rodriguez, M.D., "Upcoming Technology for Aortic Arch Aneurysms," Endovascular Today, Nov. 2015, pp. 46-52.

* cited by examiner

DEVICE TO TREAT VASCULAR DEFECT AND METHOD OF MAKING THE SAME

CROSS-REFERENCE TO RELATED APPLICATIONS

This application claims priority to U.S. Provisional Application No. 62/620,696 filed on 23 Jan. 2018, the contents of which are incorporated herein by reference.

BACKGROUND OF THE INVENTION

The present invention relates to a device to treat a vascular defect. More specifically, the invention relates to devices for treating aneurysms, dissections and other structural abnormalities of the vasculature.

An aneurysm may be defined as a blood-filled bulge in the wall of a blood vessel. As an aneurysm increases in size, the risk of clotting or rupture increases, and rupture is often fatal. Although they may occur in any blood vessel, aneurysms in the aorta, particularly thoracic aortic aneurysms and abdominal aortic aneurysms are particularly dangerous. Such aneurysms are often treated by insertion of a vascular device at the position of the aneurysm. The tubular device is inserted into the blood vessel so as to provide support to the weakened wall of the blood vessel, thus preserving the flow of blood in the parent vessel, and disrupting the blood flow to the aneurysm. As a result, intra-aneurysmal thrombosis occurs, followed by the shrinkage of the aneurysm. Thus, it is desired that a device to have an optimum mechanical strength in the radial direction, so as to be able to provide support to the weakened blood vessel. It is also desired for the device to have a porosity such that the flow of blood to the aneurysm is restricted, thus enabling shrinkage of the aneurysm.

A dissection may be defined as a tear in the vessel wall, with propagation of blood into the media and development of a true and false lumen separated by a flap. The flap is generally floating in the blood, and needs to be sealed for the vessel to function normally.

Vascular devices of the self-expanding type are well known in the art. Examples of self-expanding device include, for example, devices described in US patent application no. US20160030155A1 which seems to describe an intraluminal prosthesis that comprises a porous, multi-layer tubular member that includes stabilization member to stabilize the position of the prosthesis within the lumen. While U.S. Pat. No. 8,192,484B2 teaches a lumen endoprosthesis formed of a multi-layer braided framework. The vascular devices known in the art have problems of mobility and structural integrity when placed inside the lumen. The existing devices are made of a combination of fabric and metal in various configurations which do not necessarily provide the optimum and desired properties.

Therefore, there is a need in the art for a vascular device for treating vascular defects, that possesses improved properties of mechanical strength and porosity to enable a speedy and effective treatment of the vascular defect(s) without migration or movement of the device within the vasculature. Such a device can also avert endoleaks, provide stability within the vessel wall, occlude the aneurysm or the dissection and provide blood flow to the branches or bifurcations in the vessels.

SUMMARY

One embodiment of the present invention describes a device for treating a vascular defect. The device includes a braided component. The braided component includes a network of a plurality of wires having at least two different diameters and wherein the network of wires includes a biocompatible shape memory alloy and a noble metal.

Another embodiment of the present invention is a method of making a braided device for treating a vascular defect. The method includes, forming a braided component by interlacing a network of a plurality of wires having at least two different diameters; preferably three or more diameters; treating the braided component to remove oxide materials on the surface of the braided component to form a surface treated braided component; and coating the surface treated braided component with a metal to form the braided device.

Another embodiment of the present invention is a device for treating a vascular defect, comprising a braided component, wherein said braided component comprises a network of a plurality of wires having at least one wire formed of at least two strands of wire spooled together, and wherein said network of wires comprise a biocompatible shape memory alloy and a noble metal.

DETAILED DESCRIPTION

Figure 1:
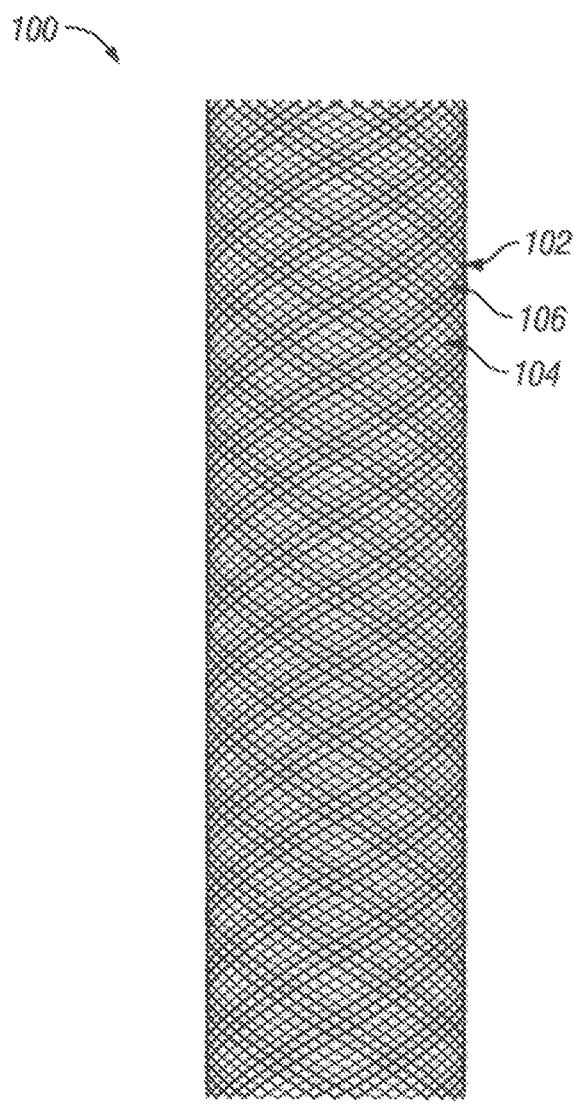
FIG. 1 is a representation of the device for treating vascular defect according to an embodiment of the invention.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

In the specification and the claims which follow, reference will be made to a number of terms which shall be defined to have the following meanings:

The singular forms "a", "an" and "the" include plural referents unless the context clearly dictates otherwise. Optional or optionally means that the subsequently described event or circumstance may or may not occur, and that the description includes instances where the event occurs and instances where it does not. "Substantially" means a range of values that is known in the art to refer to a range of values that are close to, but not necessarily equal to a certain value.

As used herein the term "aneurysm" is defined as a localized, blood filled bulge in the wall of a blood vessel.

One embodiment of the present invention describes a device for treating a vascular defect. The device includes a braided component. The braided component includes a network of a plurality of wires having at least two different diameters, and two or more wires of the same diameter bundled together before braiding and wherein the network of wires includes a biocompatible shape memory alloy and a noble metal.

Another embodiment of the present invention is a device for treating a vascular defect, describes a braided component, wherein said braided component comprises a network of a plurality of wires having at least one wire formed of at least two strands of wire spooled together, and wherein said network of wires comprise a biocompatible shape memory alloy and a noble metal.

In an example embodiment of the present invention, the device to treat vascular defect is a vascular device. In another example embodiment of the present invention, the device is a vascular device that is self-expanding type of vascular device. Self-expanding vascular devices are defined as those which can be expanded by applying heat or electricity to the device in its contracted form, as opposed to balloon-expanded devices that are expanded by inflating a balloon within the device after it is implanted in its position at the site of the vascular defect. In yet another embodiment of the present invention, the device is used to treat aneurysms in the blood vessels of an organism. In an embodiment of the invention, the device remains substantially immobile with respect to its placement in the region of the vascular defect.

In an embodiment of the present invention, the plurality of wires can have at least two different diameters, may comprise wires formed of single strands, wires formed of multiple strands spooled together, and combinations thereof. In an embodiment of the present invention, the plurality of wires may be formed from at least two to at least seventy-five strands or more spooled together.

As depicted in FIG. 1 according to an embodiment of the present invention, the device 100 includes a braided network of wires 102. In one embodiment of the present invention, the braided component may be a multi braided component. The network is produced by interlacing two (104 and 106) or more wires of different diameters 104 and 106. In one embodiment of the present invention, the wire 106 has a larger diameter than the wire 104. In another embodiment of the present invention, the wire 106 includes a bundle of at least two strands of wires wherein the diameter of the bundle of wires is greater than the diameter of the wire 104. In an example embodiment the wire 106 may be a bundle of a plurality of wires including from about two to about seventy-two or more strands of wires. Typically, the wire 106 can impart mechanical strength to the device of the present invention by forming a strengthening backbone along the entire length of the device, thus enhancing the radial strength of the device.

In one embodiment of the present invention, the wire 104 has a diameter in a range from about 0.006 inches to about 0.012 inches. The range can be from about 0.0049, 0.005, 0.0051, 0.0052, 0.0053, 0.0054, 0.0055, 0.0056, 0.0057, 0.0058, 0.0059, 0.0060, 0.0061, 0.0062, 0.0063 0.0062, 0.0063, 0.0064, 0.0065, 0.0066, 0.0067, 0.0068, 0.0069, 0.007, 0.0071, 0.0072, 0.0073, 0.0074, 0.0075, 0.0076, 0.0077, 0.0078, 0.0079, 0.008, 0.0081, 0.0082, 0.0083, 0.0084, 0.0085, 0.0086, 0.0087, 0.0088, 0.0089, 0.009, 0.0091, 0.0092, 0.0093, 0.0094, 0.0095, 0.0096, 0.0097, 0.0098, 0.0099, 0.01, 0.0101, 0.0102, 0.0103, 0.0104, 0.0105, 0.0106, 0.0107, 0.0108, 0.0109, 0.011, 0.0111, 0.0112, 0.0113, 0.0114, 0.0115, 0.0116, 0.0117, 0.0118, 0.00119, 0.0012, 0.00121, 0.00122, 0.00123, 0.00124, and about 0.00125 inches, and intervals therein. In another embodiment of the present invention, the wire 106 has a diameter in a range from about 0.002 inches to about 0.009 inches. The range can be from about 0.0015, 0.0016. 0.0017, 0.0018. 0.0019, 0.002, 0.0021, 0.0022, 0.0023, 0.0024, 0.0025, 0.0026, 0.0027, 0.0028, 0.0029, 0.0030, 0.0031, 0.0032, 0. 0.0032, 0.0033, 0.0034, 0.0035, 0.0036, 0.0037, 0.0038, 0.0039, 0.004, 0.0041, 0.0042, 0.0043, 0.0044, 0.0045, 0.0046, 0.0047, 0.0048, 0.0049, 0.005, 0.0051, 0.0052, 0.0053, 0.0054, 0.0055, 0.0056, 0.0057, 0.0058, 0.0059, 0.006, 0.0061, 0.0062, 0.0063, 0.0064, 0.0065, 0.0066, 0.0067, 0.0068, 0.0069, 0.007, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.009, 0.0091, 0.0092, 0.0093, 0.0095, 0.0096, 0.0097, 0.0098, and about 0.0099 inches, and intervals therein. In another embodiment of the present invention, the wire 106 has a diameter in a range from about 0.0017 inches to about 0.009 inches. The diameter can be from about 0.0017, 0.0018, 0.00185, 0.00190, 0.00191, 0.00192, 0.00193, 0.00194, 0.00195, 0.00196, 0.00197, 0.00198, 0.00199, 0.002, 0.0025, 0.003, 0.0035, 0.004, 0.0045, 0.005, 0.0055, 0.006, 0.0065, 0.007, 0.0075, 0.008, 0.0085, 0.009, 0.0095, and 0.01 inches. As shown in FIG. 1 the wire 104 may be braided into a tightly braided or loosely braided structure so as to control the porosity of the braided structure. The porosity of the device can be maintained at an optimal value to effectively to treat the vascular defect. In one embodiment of the present invention, the device 100, can have a porosity in a range from about 30 percent to about 90 percent. In another embodiment of the present invention, the device 100, can have a porosity in a range from about 25 percent to about 80 percent.

In an embodiment of the present invention, the outer surface and the inner surface of the device may have different textures. In one embodiment of the present invention, the outer surface is less smooth as compared with the inner surface. In one embodiment of the present invention the average roughness of the outer surface is in a range from about 30 microns to about 90 microns, and the average roughness of the inner surface is in a range from about 5 microns to about 15 microns. Typically, the roughness of the outside layer can be created by using the pitch angle of the braid and the resultant braid structure which is programmed to give radial strength with the bundle of wires and the other wires of different diameter to provide porosity. The pitch angle of the braid is defined as the angle made by the strand of the braid with the axis of the braided network.

In an embodiment of the present invention, the device having a rough outer surface in comparison to the smooth texture of the inner surface, which aids in the device being immobilized from its position at the point of the vascular defect. In another embodiment of the present invention, the device is a self-expanding device, thereby, the friction between the outer surface of the device and the wall of the lumen ensures that the device is not displaced from its intended position, while the smooth inner surface of the device provides minimal resistance to the flow of blood through the device.

In an embodiment of the present invention, the device is made of a biocompatible material. In another embodiment of the present invention, the device is made of shape memory alloys. In another embodiment of the present invention, the device is made of a shape memory alloy composed of an alloy of nickel and titanium. Non-limiting examples of shape memory alloys include alloys of nickel and titanium, stainless steel, titanium, tungsten, and noble metals including, but not limited to, platinum, gold, and silver. In a preferred embodiment of the present invention, the shape memory alloy includes nickel and titanium. In another preferred embodiment of the present invention, the shape memory alloy includes Nitinol®. Non-limiting examples of such biocompatible shape memory alloys include nickel-titanium alloy known by the trade name Nitinol®, stainless steel, titanium, tungsten, platinum, gold, silver, etc.

In another embodiment of the present invention, the vascular device has a plurality of loops on at least one of its ends. In another embodiment of the invention, the vascular device has a plurality of loops at both its ends. The loops may be formed by joining the ends of the wires that are braided to form the network of wires. Alternatively, in another embodiment of the present invention, the loops may be formed and bonded to the braided component by means of a bonding process. Non-limiting examples of the bonding process may include welding, suturing and the like.

In an embodiment of the present invention, the pitch angle can be from about 60° to about 150°. In another embodiment of the present invention, the pitch angle can be from about 100° to about 130°. In another embodiment of the present invention, the pitch angle can be 118.7°.

Figure 2:
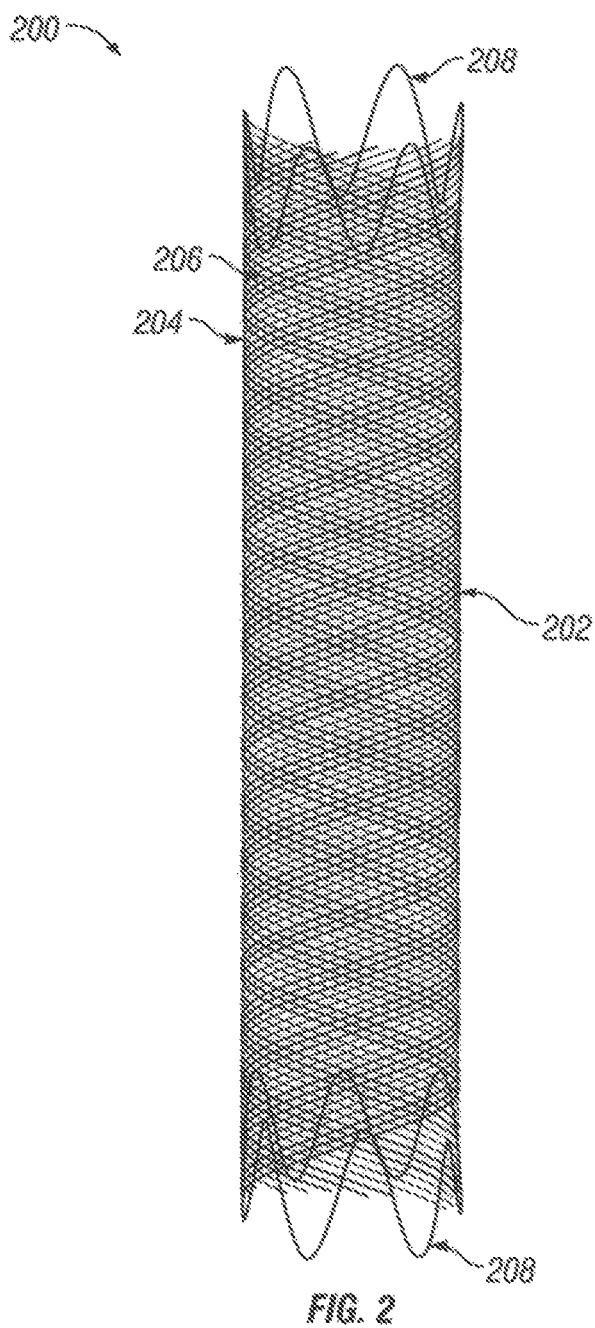
FIG. 2 is a representation of the device for treating vascular defect according to an embodiment of the invention.

As depicted in FIG. 2 according to an embodiment of the present invention, the device 200 of the invention includes a braided network of wires 202 produced by interlacing two wires 204 and 206. The network of wires 202 has a plurality of loops 208 at least one of the ends of the braided network of wires 202. The presence of the loops 208 at least one of the end of the braided network 202 aids in anchoring the device 200 at its intended position. The chances of stretching of the device 200 while being implanted is reduced by the presence of the loops 208, thus ensuring that the porosity of the device 200 is not affected.

Another embodiment of the present invention is a method of making a braided device for treating a vascular defect. The method includes, forming a braided component by interlacing a network of a plurality of wires having at least two different diameters; treating the braided component to form a treated braided component. Treating the braided component to remove an oxide material to form a treated braided component. The method further includes the step of coating the treated braided component with a noble metal to form the braided device.

In an embodiment of the method of making a braided device according to the present invention, the plurality of wires having at least two different diameters may comprise wires formed of single strands, wires formed of at least two strands of wire spooled together, and combinations thereof. In an embodiment of the present invention, the wires may be formed of from at least two to at least seventy five strands or more spooled together.

Figure 3:
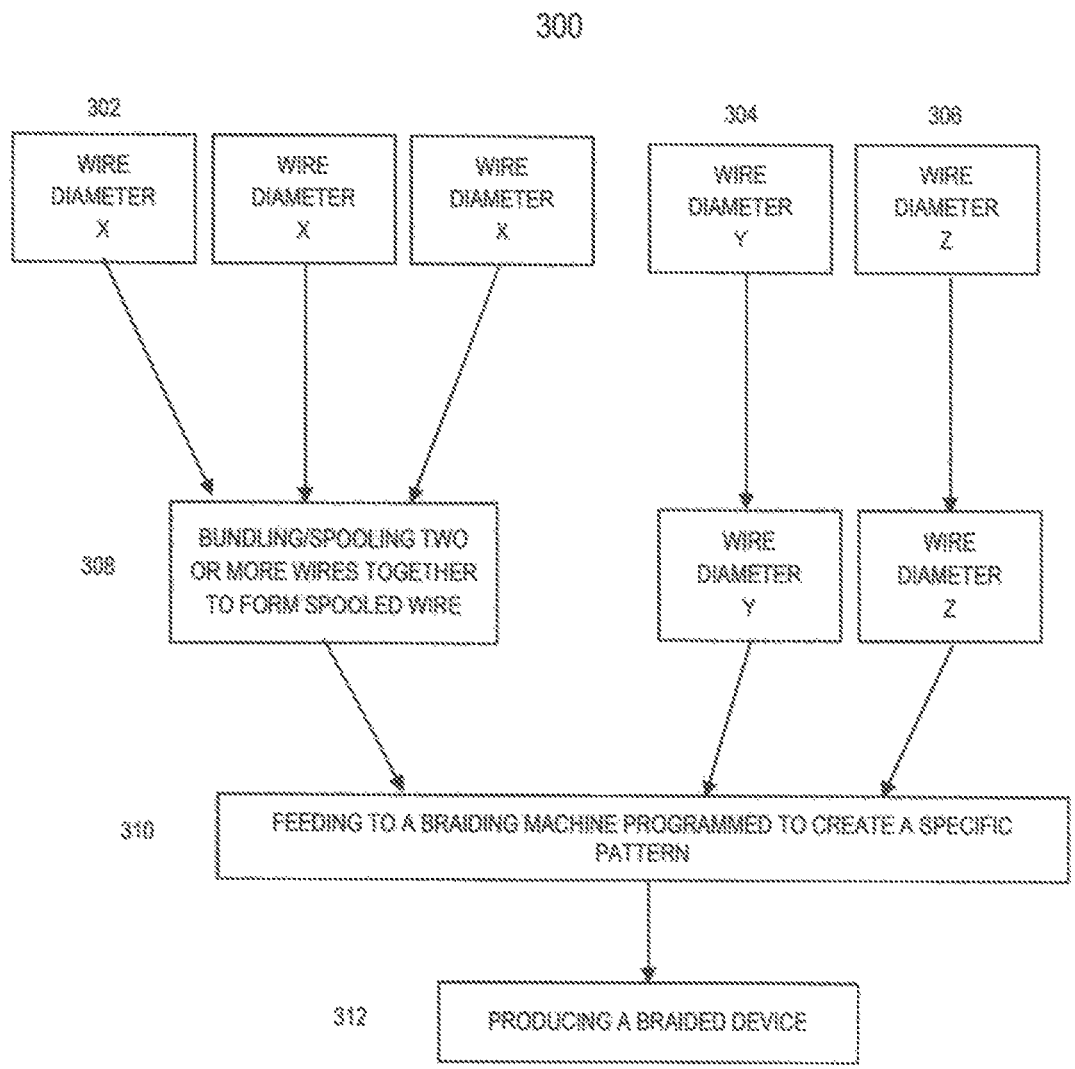
FIG. 3 is a flowchart describing the method of making the device for treating vascular defect according to an embodiment of the invention.

In an embodiment of the method 300 of making the braided device, referring to FIG. 3, the method includes the step of spooling/bundling 308 at least two strands of wires 302 of diameter X to form a spooled wire. The method further includes the step of feeding 310 two or more wires 304 and 306 of diameters Y and Z respectively and the spooled wires obtained in step 308, to a braiding machine that is programmed to create a specific pattern, and the step of producing 312 a braided device of the invention. In an example embodiment of the present invention, the braided device 100 may be braided with wires having at least four different diameters. In another embodiment of the present invention, the braided device may be braided with wires having at least five different diameters. In another embodiment of the present invention, the braided device may be braided with wires having at least seven different diameters. In an embodiment of the present invention, the at least two strands of wires 302 of diameter X have the same diameter. In an embodiment of the present invention, the at least two strands of wires 302 of diameter X have different diameters. In an embodiment of the present invention, the two or more wires 304 and 306 of diameters Y and Z respectively may have the same diameter. In an embodiment of the present invention, the two or more wires 304 and 306 of diameters Y and Z respectively may have different diameters. In an embodiment of the present invention, the wires 302, 304, 306 may all have the same diameter. In an embodiment of the present invention, the wires 302, 304, 306 may all have different diameters.

In one embodiment of the present invention, three individual spools of wire having a diameter of about 0.006 inches Nitinol wires are taken along with three other individual spools of wire having a diameter of about 0.007 inches, or wire having a diameter of about 0.008 inches, or wire having a diameter of about 0.009 inches wires. In an example embodiment the three spools of wire having a diameter of about 0.006 inches wires are combined together into a one spool herein referred to as "single spool", such that each wire now has three strands having a diameter of about 0.006 inches of wires rolled into the single spool. The single spool is then fed into the braiding machine (either 48 spool machine, 86 spool machine). Several single spools having the three strand wire may be produced. The single spools may include individual strands of wire having a diameter of about 0.007 inches, or about 0.008 inches or about 0.009 inches are created to feed enough wire into braiding machine. Depending on the pitch angle that is used to braid all the several single spools together to attain a resultant property of the braid that creates the unique structure.

In one embodiment of the present invention the surface of the device is treated to remove any oxide present on the surface. The surface of the braid made from a multiple combination of wires has a very rich oxide content which can be to be removed before the noble metal coating is bonded to the surface. In one embodiment of the present invention, the oxide layer is removed by mechanical polishing, electrochemical removal process or a combination thereof. In another embodiment of the present invention, the oxide layer can be removed by a combination of mechanical polishing, electrochemical removal process. In yet another embodiment of the present invention, about less than 0.0002 inches of the material can be removed, such that only the outermost oxide layer is removed. The oxide layer removed can be about 0.0005, 0.00049, 0.00048, 0.00047, 0.00046, 0.00045, 0.00044, 0.00043, 0.00042, 0.00041, 0.0004, 0.00039, 0.00038, 0.00037, 0.00036, 0.00035, 0.00034, 0.00033, 0.00032, 0.00031, 0.0003, 0.00029, 0.00028, 0.00027, 0.00026, 0.00025, 0.00024, 0.00023, 0.00022, 0.00021, 0.0002, 0.00019, 0.00018, 0.00017, 0.00016, 0.00015, 0.00014, 0.00013, 0.00012, 0.00011, and 0.0001 inches in thickness. The oxide free layer can then be coated with a nano-layer of noble metal using methods known in the art, such as by metal deposition that can include, but is not limited to, processes such as plasma deposition, chemical vapor deposition etc. In an embodiment of the present invention, the noble metal can be platinum, silver, gold or combinations thereof.

Generally, the thickness of the platinum coating is such that it does not affect the shape memory property of the device. In one embodiment of the present invention, the coating of platinum provides radio-opacity to the device, making the implantation and monitoring of the device easier. The platinum layer also enhances the biocompatibility and corrosion resistance of the device. In an example embodiment of the present invention, the thickness of the platinum layer may be in a range from about 3 Angstroms and about 10 Angstroms. In another example embodiment of the present invention, the thickness of the platinum layer may be in a range from about 4 Angstroms to about 8 Angstroms. In yet another example embodiment of the present invention, the layer of platinum is nano-infused into the metal alloy.

EXAMPLES

A braided component according to an embodiment of the present invention was fabricated with nitinol wires. Five wires of diameter sizes were used to form the braid: 0.008 inches, 0.010 inches, 0.012 inches, 0.014 inches and 0.016 inches. Two sets of seven wires of diameters 0.010 inches, 0.010 inches, 0.014 inches, 0.014 inches, 0.008 inches, 0.014 inches, and 0.012 inches, respectively and seven wires of diameters 0.012 inches, 0.016 inches, 0.016 inches, 0.008 inches, 0.008 inches, 0.016 inches and 0.010 inches were braided and this process repeated 6 times. The braided device was formed by braiding together a total of 84 wires, to produce a braided device of length 300 mm and diameter 33.83 mm. The pitch angle was 118.6°.

A braided component according to an embodiment of the present invention was fabricated with nitinol wires. A braided network of wires was produced by interlacing a first set of wires and a second set of wires. The first set of wires included five wires of diameters 0.008 inches, 0.010 inches. 0.012 inches, 0.014 inches and 0.016 inches were used. The second set of wires included seven wires of diameters 0.010 inches, 0.010 inches, 0.014 inches, 0.014 inches, 0.008 inches, 0.014 inches and 0.012 inches were employed. This process repeated 6 times. The braided device was formed by braiding together a total of 84 wires, to produce a braided device of length 300 mm and diameter 33.83 mm. The pitch angle was 118.6°.

The invention claimed is:

1. A device for treating a vascular defect, comprising:
a braided component having an outer surface and an inner surface, wherein said braided component comprises a network of wires having at least two different diameters, wherein the outer surface has an average roughness from about 30 microns to about 90 microns, the inner surface has an average roughness from about 5 microns to about 15 microns, wherein the wires of different diameters provide porosity, and wherein said network of wires comprises a biocompatible shape memory alloy and a noble metal.

2. The device of claim 1, wherein said wires having at least two different diameters comprises wires formed of a single strand of wire, wires formed of at least two strands of wire spooled together, or combinations thereof.

3. The device of claim 1, wherein said device remains substantially immobile with respect to its placement in a region of the vascular defect.

4. The device of claim 1, wherein said shape memory alloy is composed of an alloy of nickel and titanium.

5. The device of claim 1, wherein said shape memory alloy is nitinol.

6. The device of claim 1, wherein said noble metal is platinum.

7. The device of claim 1, further comprising plurality of loops located at at least one end of the braided component.

8. A method of making the device of claim 1 comprising:
forming the braided component by interlacing the network of wires, wherein the network of wires forms the outer surface;
treating the braided component to remove any oxidized material on the outer surface; and
coating the outer surface with a metal to form the braided component.

9. The method of claim 8, wherein treating is by mechanical polishing, an electrochemical removal process, or combinations thereof.

10. The method of claim 8, wherein coating is by noble metal deposition.

11. The method of claim 10, wherein the noble metal is nano-infused into the alloy.

12. The method of claim 8, wherein said wires having at least two different diameters comprises wires formed of single strands, wires formed of at least two strands of wire spooled together, and combinations thereof.

13. The method of claim 8, wherein the network of wires comprises wires comprising at least two different diameters.

14. The method of claim 8, wherein the network of wires comprises wires comprising at least three different diameters.

15. The method of claim 8, wherein the metal coating the outer surface comprises a noble metal.

16. The method of claim 15, wherein the noble metal is platinum, silver, gold or combinations thereof.

17. The method of claim 16, wherein the noble metal is platinum.

18. The device of claim 1, wherein the braided component comprises a pitch angle of from about 60° to about 150°.

19. The device of claim 18, wherein the pitch angle creates the average outer surface roughness.

20. A device for treating a vascular defect, comprising:
a braided component, wherein said braided component comprises a network of a plurality of wires having at least one wire formed of at least two strands of wire spooled together, wherein the at least two strands of wire comprise different diameters, wherein the braided component has an average outer surface roughness and porosity, an average inner surface roughness and porosity, wherein the average outer surface roughness is greater than the average inner surface roughness, and wherein said network of wires comprises a biocompatible shape memory alloy and a noble metal.

* * * * *